United States Patent
Procunier et al.

(12) 
(10) Patent No.: US 6,197,518 B1
(45) Date of Patent: Mar. 6, 2001

(54) MARKERS FOR FUSARIUM HEAD BLIGHT (FHB) DISEASE RESISTANCE

(75) Inventors: James Douglas Procunier; Jeannie Gilbert; T. Fred Townley-Smith, all of Manitoba; Ken Armstrong; George Fedak, both of Ontario, all of (CA)

(73) Assignee: Her Majesty the Queen in right of Canada, as represented by the Department of Agriculture (CA)

( * ) Notice: Subject to any disclaimer, the term of this patent is extended or adjusted under 35 U.S.C. 154(b) by 0 days.

(21) Appl. No.: 09/334,654

(22) Filed: Jun. 17, 1999

(51) Int. Cl.[7] ........................................................ C12Q 1/68

(52) U.S. Cl. .............................................. 435/6; 435/91.2

(58) Field of Search ........................................ 435/6, 91.2

(56) References Cited

FOREIGN PATENT DOCUMENTS

WO 97/01567 * 1/1997 (WO) .

* cited by examiner

Primary Examiner—Remy Yucel
(74) Attorney, Agent, or Firm—Michael Williams; Adrian D. Battison

(57) ABSTRACT

The chromosomal location of Fusarium head blight (FHB) resistance genes in wheat and the discovery of molecular markers for detecting the presence of these genes is herein described. The markers are generated via PCR or similar amplification reaction using primers identified herein. As a result, seed material can be assayed, thereby eliminating the time and cost involved in assaying adult plants for FHB resistance. Furthermore, the markers allow for gene pyramiding of the multiple, independent resistance genes into complex genetic backgrounds. In addition, the markers can be assayed in parallel. Finally, the markers are cost effective, highly reliable and accurate, and require just a few hours for testing.

4 Claims, 9 Drawing Sheets

FIGURE 1: Genetic Variance Map of FHB Molecular Markers

Proportion of Genetic Variance of Spray Inoculation Ratings
Using Mean Ratings

| | Fhb1 | WMS389 | | | |
|---|---|---|---|---|---|
| Individual = | 31% | | | | Chromosome 3BS |
| Individual = | | 15% | | | |
| | | bcd907a | Dual Assoc. 51% | Dual | |
| | Fhb2 | 6B NOR | | Assoc. | Chromosome 6BS |
| Individual = | | 20% | | 56% | |
| | | | Dual Assoc. 52% | | |
| | WMS126 | Fhb3 | B1 | | |
| Individual = | 28% | 25% | | | Chromosome 5AL |
| | Dual Assoc. 37% | 19.5 cM | | | |

Total variance
Individual variances added =    79%  Using WMS389, 6B NOR, WMS126
All markers used sumultaneously =   64%

Proportion of Genetic Variance of Injection Inoculation Ratings
Using Mean Ratings

| | Fhb1 | WMS389 | | | |
|---|---|---|---|---|---|
| Individual = | 58% | | | | Chromosome 3BS |
| Individual = | | 38% | | | |
| | | bcd907a | Dual Assoc. 74% | Dual | |
| | Fhb2 | 6B NOR | | Assoc. | Chromosome 6BS |
| Individual = | | 21% | | 90% | |
| | | | Dual Assoc. 60% | | |
| | WMS126 | Fhb3 | B1 | | |
| Individual = | 26% | 34% | | | Chromosome 5AL |
| | Dual Assoc. 37% | 19.5 cM | | | |

Total variance
Individual variances added =    105%  Using WMS389, 6B NOR, WMS126
All markers used sumultaneously =   171%

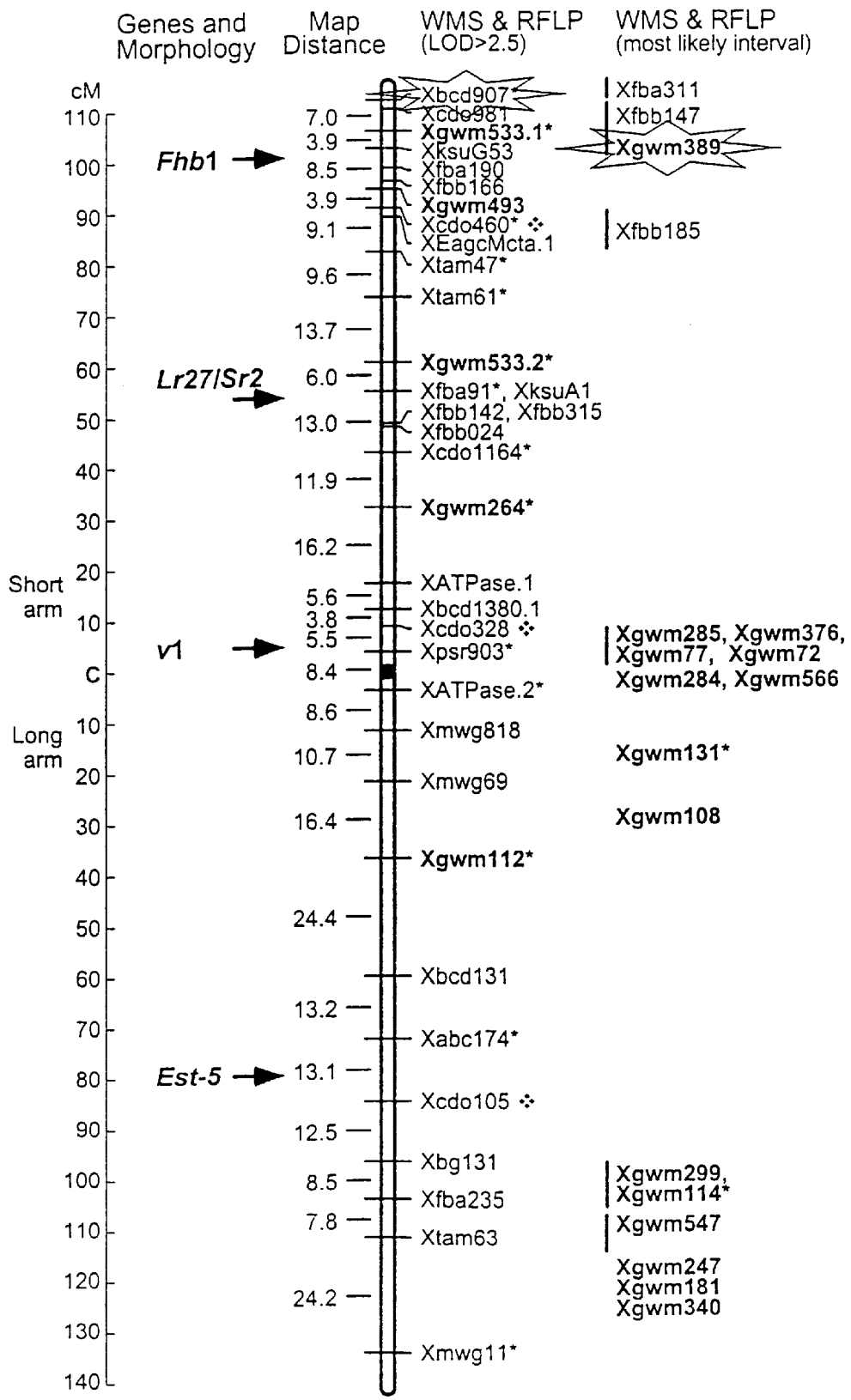
FIGURE 2: Genetic Map of Chromosome 3B

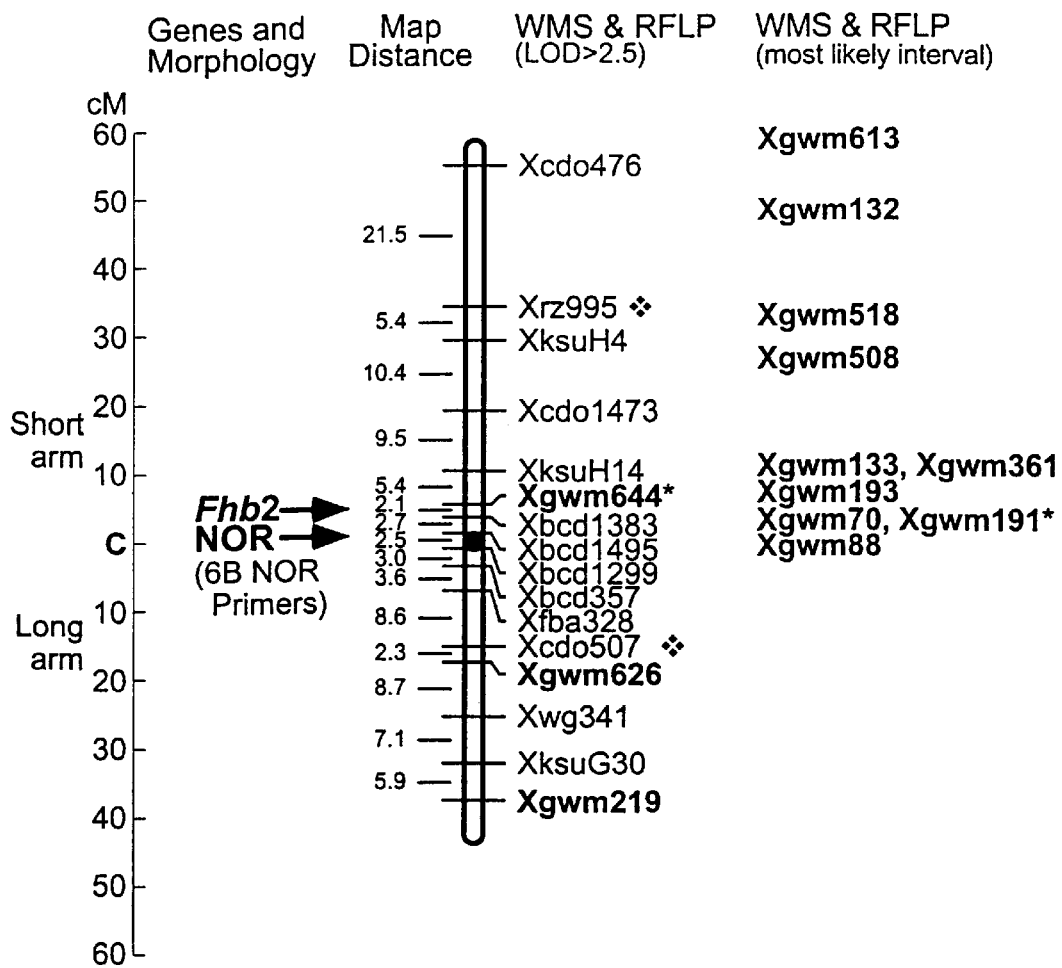

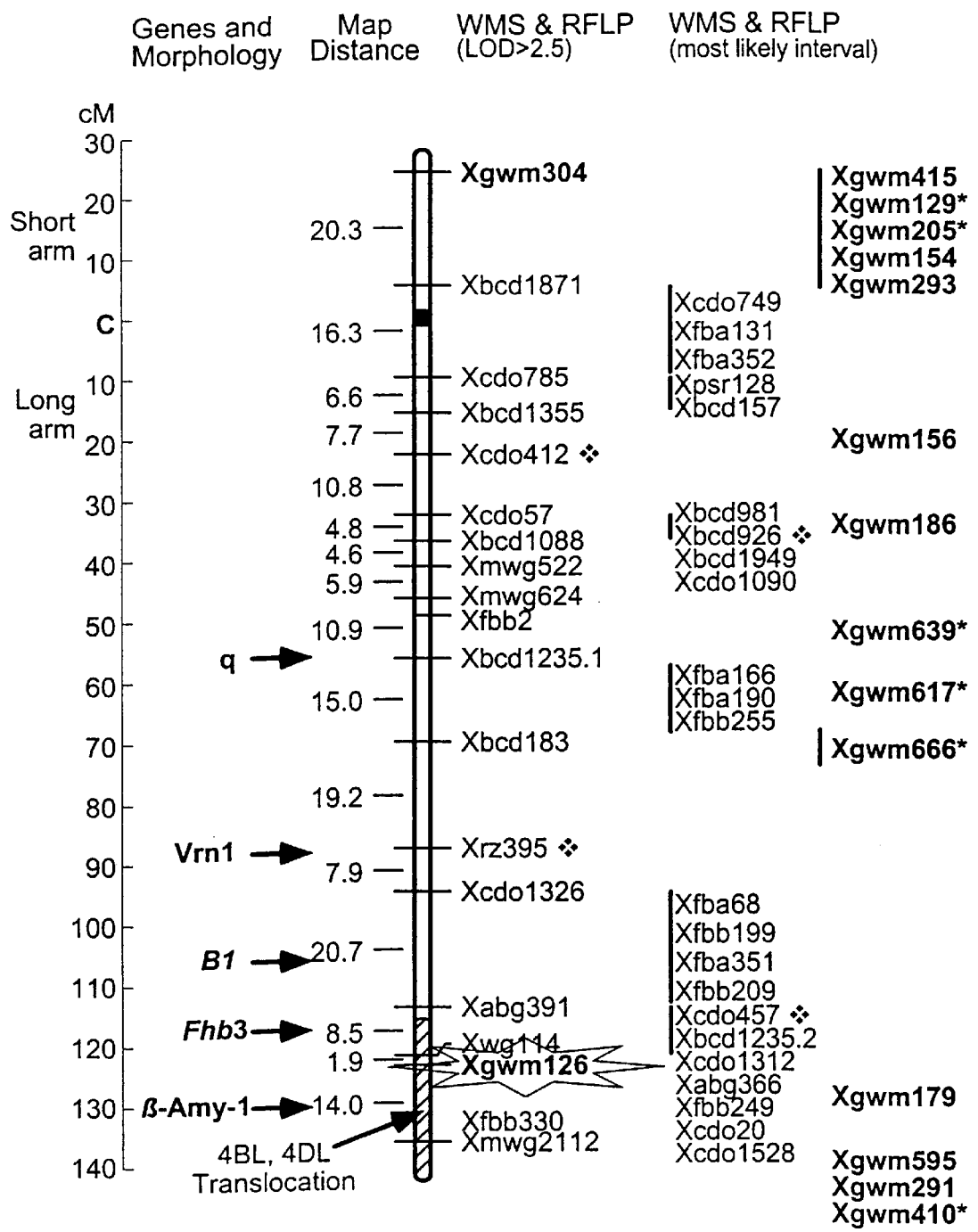
FIGURE 4: Genetic Map of Chromosome 5A

FIGURE 5: 6B NOR Primers
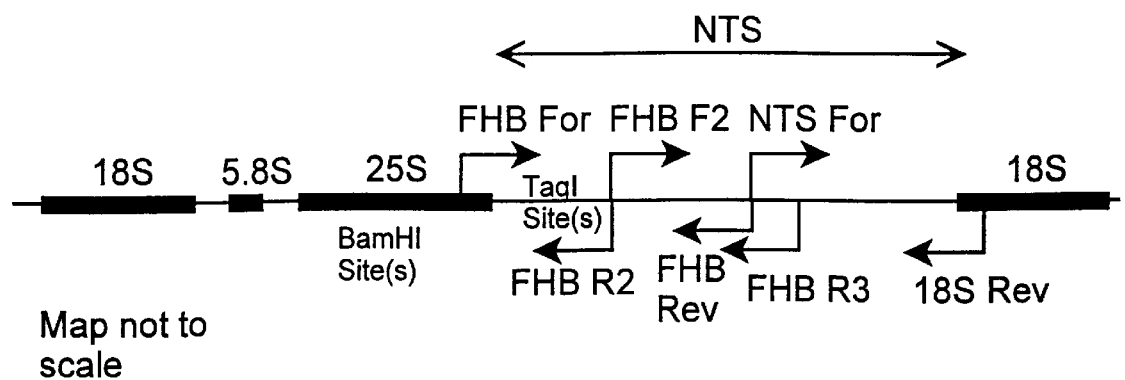
Map not to scale

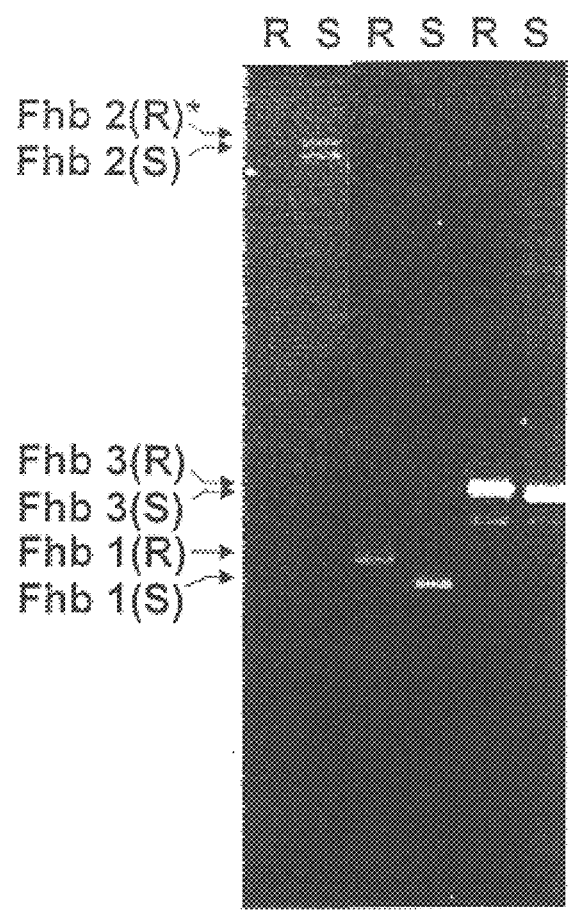
Figure 6: FHB Codominant molecular markers (Fhb1, Fhb2, Fhb3)

Figure 7: Multiplex Markers of FHB Resistance Genes
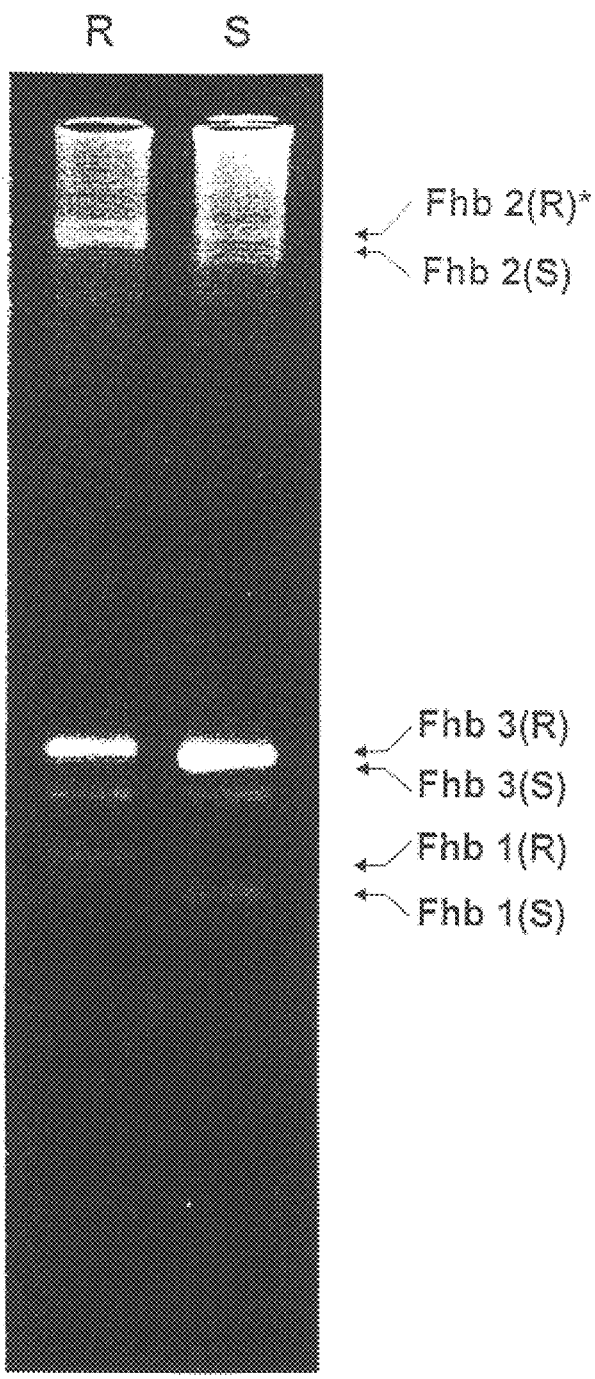
* Fhb 2(R) band on PAGE gels

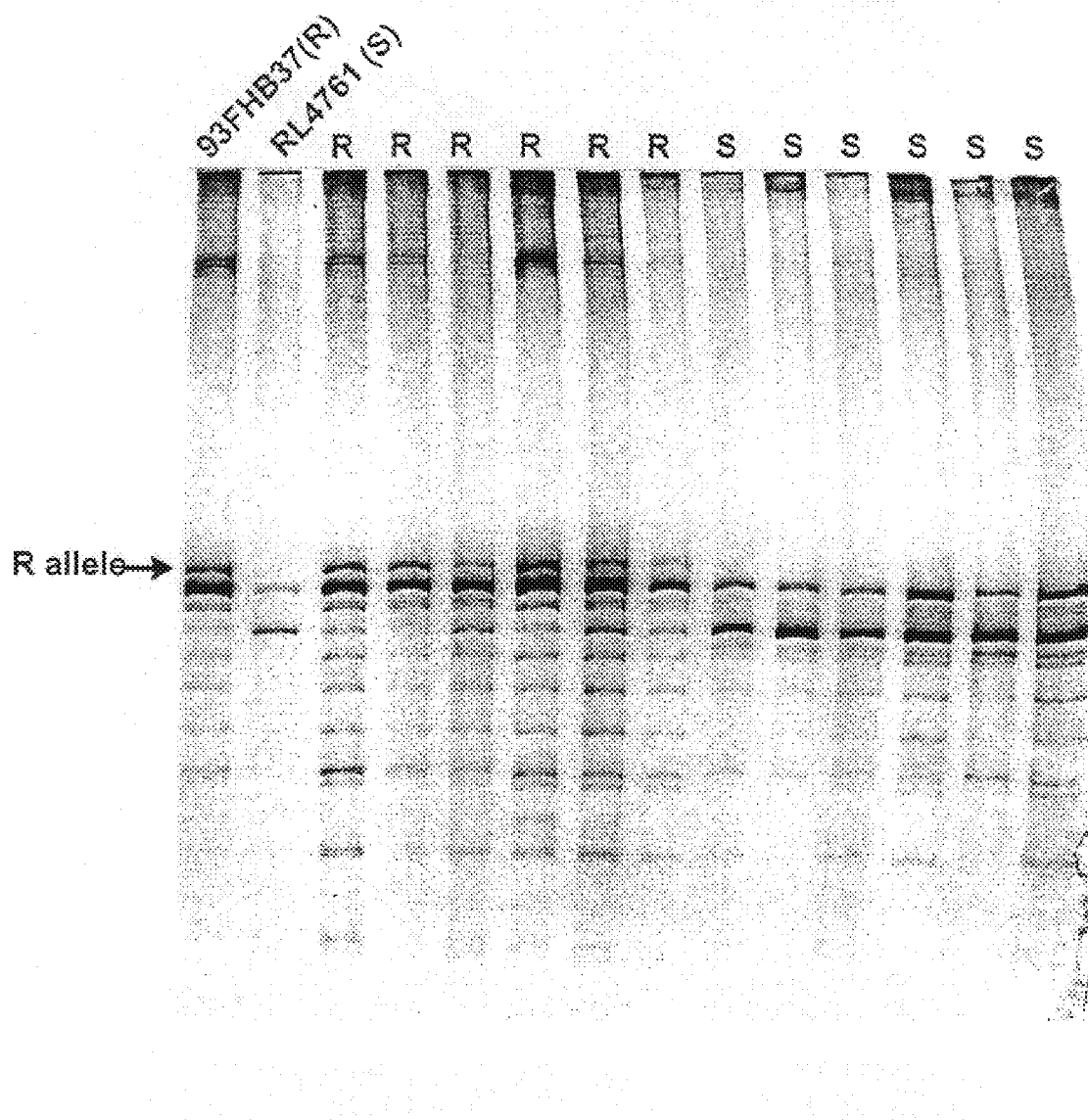
Figure 8: Segregation of Fhb 2 (R) allele in doubled haploid progeny on 6% PAGE gel

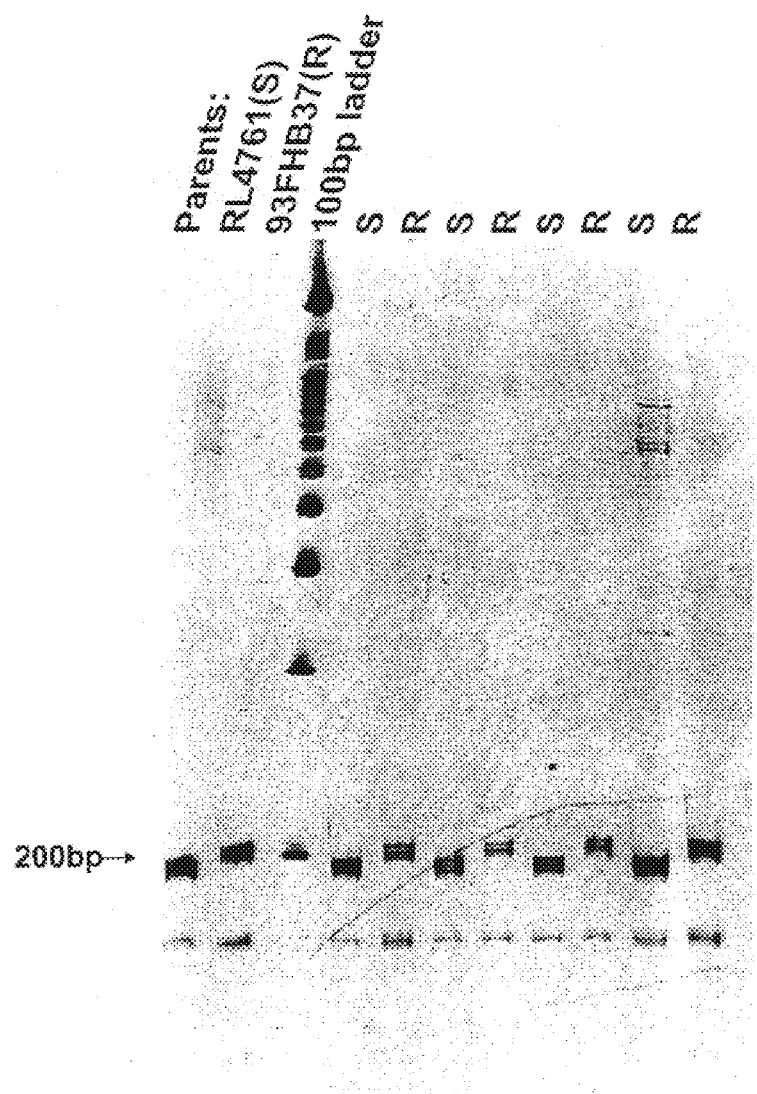
Figure 9: Segregation of Fhb 3 codominant molecular markers on mini-sequencing gel in doubled haploid progeny

MARKERS FOR FUSARIUM HEAD BLIGHT (FHB) DISEASE RESISTANCE

FIELD OF THE INVENTION

The present invention relates generally to the fields of agriculture and disease resistance. More specifically, the present invention relates to markers for Fusarium head blight disease resistance.

BACKGROUND OF THE INVENTION

Fusarium Head Blight (FHB) or scab of wheat is a fungal disease of the genus Fusarium that affects crops such as wheat, oats, barley, rye, corn and some grasses. The disease is of great interest, as it can have significant effects on crop yields. For example, the damage caused by the fungus *Fusarium graminearum* on wheat can be enormous. In particular, during 1993, this fungus caused an estimated three billion dollar loss to farmers in North America alone. The main effects of FHB infection are reduced crop yield and grain quality. Furthermore, FHB also produces mycotoxins which makes contaminated grain unsuitable for human or livestock consumption, for example, causing livestock feeding problems, such as refusal of feed or vomiting.

In order for this disease to occur, a susceptible host must be present and the environmental conditions must be favourable for infection and disease development. Since the environmental conditions cannot be controlled on a large scale, incorporating resistance genes into adapted wheat varieties is the most effective, economic and environmentally safe means of controlling the disease.

Naturally-occurring FHB-resistant cultivars of wheat are known and have been reported as two to three independently segregating genes in some Chinese and Brazilian strains (Van Ginkel et al., 1996, *Plant Disease* 80:863). Unfortunately, these resistant cultivars have undesirable agronomic traits, such as small heads and late maturation, and are therefore of little commercial value. However, the resistant cultivars have been used as parents in breeding programs with elite lines (Bai and Shaner, 1994, *Plant Disease* 78:760–765), with limited success. This is due to the fact that the inheritance of resistance to FHB is quantitative and controlled by many additive genes. As a consequence, data elucidating both the number and location of these genes has been problematic.

Hexaploid wheat is comprised of three homoeologous genomes (A, B, and D) each having 7 chromosomes. Procunier et al. 1998, $9^{th}$ Int. Wheat Gen.Symp., Sask. SK.3:143–147 reported that the D genome ( chromosomes D1 to D7) lacked any significant FHB resistance genes. This placed the resistance genes on the A or B genomes. Two genetic regions ( 3BS and 6BL) for FHB resistance were identified by Anderson et al., 1998, National Scab Forum, St. Paul, Minn. and a single region ( 5A or 6B) is associated with the phenotypic marker awnless and FHB resistance( Ban et al. 1997, Fifth European Fusarium Seminar, Szeged, Hungary). However, Buerstmayr has recently showed that chromosomes 6D, 6B, 5A 4D, and 7A contain the FHB resistance genes ( Buestmayr et al., 1999, Theor. Appl Genet. 98:76–85).

Clearly, identification of the chromosomal locations of the FHB resistance genes followed by molecular mapping of these genes would greatly facilitate breeding FHB resistant strains. Specifically, molecular marker based-assays could be done on seed material, thus eliminating the lengthy growing time for assaying adult plants. Furthermore, seed testing does not require growth cabinet space or a costly nursery. The markers would also allow for gene pyramiding of multiple, independent resistance genes into complex genetic backgrounds. Ideally, the markers should be cost effective, highly reliable and accurate and require only a few hours for testing.

SUMMARY OF THE INVENTION

It is therefore an object of the invention to provide molecular markers for FHB resistance genes.

According to a first aspect of the invention, there is provided a method of detecting Fusarium head blight resistance in a wheat cell, said method comprising:

providing genomic DNA extracted from the wheat cell;

providing a primer set selected from the group consisting of:

primer set A: a forward primer selected from the group consisting of: Forward Fhb1 primer (SEQ ID No. 1), contiguous primers thereof, noncontiguous primers thereof and homologous primers thereof; and a reverse primer selected from the group consisting of: Reverse Fhb1 primer (SEQ ID No. 2), contiguous primers thereof, noncontiguous primers thereof and homologous primers thereof; or primer set B: a forward primer selected from the group consisting of: Forward Fhb2 primer (SEQ ID No. 3), contiguous primers thereof, noncontiguous primers thereof and homologous primers thereof; and a reverse primer selected from the group consisting of: Reverse Fhb2 primer (SEQ ID No. 4), contiguous primers hereof, noncontiguous primers thereof and homologous primers thereof; or primer set C: a forward primer selected from the group consisting of: Forward Fhb3 primer (SEQ ID No. 5), contiguous primers thereof, noncontiguous primers thereof and homologous primers thereof; and a reverse primer selected from the group consisting of: Reverse Fhb3 primer (SEQ ID No. 6), contiguous primers thereof, noncontiguous primers thereof and homologous primers thereof; or combinations of primer set A, primer set B and primer set C.

combining the genomic DNA and the primer set with reagents suitable for DNA amplification, thereby forming a reaction mixture;

incubating the reaction mixture under conditions wherein the DNA is amplified, thereby producing a DNA fragment of a given molecular weight; and determining the molecular weight of the DNA fragment, wherein use of primer set A results in synthesis of a DNA molecule of a first molecular weight when Fhb1 is present on the genomic DNA or the synthesis of a DNA molecule of a second molecular weight when Fhb1 is absent on the genomic DNA; use of primer set B results in synthesis of a DNA molecule of a third molecular weight when Fhb2 is present on the genomic DNA or the synthesis of a DNA molecule of a fourth molecular weight when Fhb2 is absent on the genomic DNA; and use of primer set C results in synthesis of a DNA molecule of a fifth molecular weight when Fhb3 is present on the genomic DNA or the synthesis of a DNA molecule of a sixth molecular weight when Fhb3 is absent on the genomic DNA The molecular weights of the DNA fragments may be determined by loading the reaction mixture onto a suitable support and electrophoresing the reaction mixture; and visualizing the banding pattern of the DNA fragments, wherein the presence of Fhb1 produces a first banding pattern while the absence of Fhb1 produces a second banding pattern, the presence of Fhb2 produces a third banding pattern while the absence of Fhb2 produces a fourth banding pattern, and the presence of Fhb3 produces a fifth banding pattern while the absence of Fhb3 produces a sixth banding pattern.

The wheat cell may be a seed.

The DNA in the reaction mixture may be digested with a restriction enzyme.

According to a second aspect of the invention, there is provided a vector arranged for transformation into wheat cells, said vector including an isolated DNA segment comprising a section of the wheat genome coding for resistance to Fusarium head blight selected from the group consisting of:

a segment of wheat chromosome 3B including Fhb1 Forward primer (SEQ ID NO. 1);
a segment of wheat chromosome 3B including Fhb1 Reverse Primer (SEQ ID NO. 2);
a segment of wheat chromosome 6B including Fhb2 Forward Primer (SEQ ID NO. 3);
a segment of wheat chromosome 6b including Fhb2 Reverse Primer (SEQ ID NO. 4);
a segment of wheat chromosome 5A including Fhb3 Forward Primer (SEQ ID NO. 5); and
a segment of wheat chromosome 5A including Fhb3 Reverse Primer (SEQ ID No. 6).

The vector may include sequences for directing replication of the vector in a wheat cell.

The vector may include sequences for directing integration of the vector into the wheat genome.

The vector may be an artificial chromosome.

According to a third aspect of the invention, there is provided a method of transferring FHB resistance to a wheat cell comprising:

providing a vector containing an isolated DNA segment comprising a section of the wheat genome coding for resistance to FHB selected from the group consisting of:
a segment of chromosome 3B including Fhb1 Forward primer (SEQ ID NO. 1);
a segment of chromosome 3B including Fhb1 Reverse Primer (SEQ ID NO. 2);
a segment of chromosome 6B including Fhb2 Forward Primer (SEQ ID NO. 3);
a segment of chromosome 6b including Fhb2 Reverse Primer (SEQ ID NO. 4);
a segment of chromosome 5A including Fhb3 Forward Primer (SEQ ID No. 5); and
a segment of chromosome 5A including Fhb3 Reverse Primer (SEQ ID No. 6), said vector arranged for replication in wheat; and
transforming said vector into the wheat cell.

BRIEF DESCRIPTION OF THE DRAWINGS

FIG. 1 is a proportion of genetic variances map for Fhb1, Fhb2 and Fhb3 resistance genes.

FIG. 2 is a map of wheat chromosome 3B.

FIG. 3 is a map of wheat chromosome 6B.

FIG. 4 Is a map of wheat chromosome 5A.

FIG. 5 is a schematic diagram of the primers tested for Fhb2 co-dominant marker.

FIG. 6 is a MetaPhor agarose gel showing the co-dominant markers for Fhb1, Fhb2 and Fhb3 as detected in resistant (R, FHB#37) and susceptible (S, RL4761)lines.

FIG. 7 is a MetaPhor agarose gel showing the multiplexed PCR markers for Fhb1, Fhb2 and Fhb3.

FIG. 8 is a PAGE gel showing the segregation of the $Fhb2^R$ allele in doubled haploid progeny.

FIG. 9 is a mini-DNA sequencing gel showing the segregation of the Fhb3 R and S alleles in doubled haploid progeny.

TABLE 1 is a partial list of the phenotypic data from the RL4761 X FHB#37 cross.

TABLE 2 is a partial list of the phenotypic data from the RL4761 X FHB#37 cross.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

The term "PCR" as used herein refers to the polymerase chain reaction method of DNA amplification. As will be understood by one knowledgeable of the art, this term also includes any and all other methods known in the art for nucleic acid amplification requiring an amplification target, at least one primer and a polymerase.

The term "primer" as used herein refers to a nucleic acid sequence that is derived or developed by any one or more of the following methods:

(1) the "primer" may be an exact copy of any one of the primer sequences described herein;

(2) the "primer" may be a fragment or subclone of any one of the primer sequences described herein;

(3) the primer may contain all or a portion of the DNA sequence of any one of the original primers and additional, contiguous DNA from the wheat genome. This is termed a "contiguous primer". This additional DNA is referred to as "upstream" or "downstream" of the original primer, depending on whether the contiguous DNA is from the 5' or 3' side of the original primer on the wheat genome. As is apparent to one knowledgeable in the art, the process of obtaining contiguous primers can be repeated indefinitely. For the purposes of this invention, all above-described primers are equivalent to the original primers described herein;

(4) the primer may contain a DNA sequence which is not contiguous to that of any one of the original primers; this primer is a "noncontiguous primer". It is to be understood that the sequence of the noncontiguous primer is sufficiently close to the sequence of the original primer on the wheat genome such that the results obtained with the non-contiguous primer are functionally equivalent to those obtained with the original primer.

(5) The primer may be a nucleic acid sequence which is substantially homologous to any one of the above-described primers. This is termed a "homologous primer". Such homology is based on the ability of the primer to function equivalently to the primers described herein. These primers may be prepared for example by chemical synthesis using substitution of known sequence; or (6) The primer may be an RNA version of any of the primers described above. RNA primers can be synthesized by any of the means known in the art.

The term "co-dominant marker" refers to a DNA fragment generated via PCR using a given pair of primers which yields a molecule of a given molecular weight for the resistance allele and a separate, different, DNA molecule for the susceptible allele.

Described herein is the chromosomal mapping of genes encoding FHB resistance in wheat. Chromosomal mapping was done by crossing a resistant (donor) strain with a susceptible strain and then determining genetic linkage between FHB resistance and a number of genetic markers, both phenotypic and molecular, as described below. The results indicate that there are three genes encoding FHB resistance located on chromosomes 3B (Fhb1), 5A (Fhb3) and 6B (Fhb2). Using this data, co-dependent molecular markers for the FHB resistance genes Fhb1, Fhb2 and Fhb3 were developed. As a result, the phenotype for FHB disease (susceptible or resistant) at these three loci of a given cultivar can quickly and easily be determined using PCR. Specifically, PCR amplification using the primers disclosed herein produces a band of a given molecular weight or a particular banding pattern when the target DNA is from a FHB-resistant strain and a band of a different molecular weight or a different banding pattern when the target DNA is from a FHB-susceptible strain.

In addition, the localization of the genes encoding FHB resistance allows for the construction of integrating and/or replicating vectors for transmitting FHB resistance genes under the control of their respective native promoter. Specifically, the regions of the wheat genome encoding FHB resistance genes can be subcloned into replicating plasmids or integrating plasmids for expression of FHB resistance under native promoter control and then transformed into suitable hosts. In this manner, FHB resistance could be transmitted to susceptible strains without crossing the susceptible strain with a resistant strain. Furthermore, it is likely that a strain containing a higher copy number of the FHB resistance genes would be more resistant to FHB infection than a strain containing single copies of the FHB resistance genes.

EXAMPLE I—INOCULUM PREPARATION

Fusarium Head Blight (FHB) inoculum is made by plating surface sterilized Fusarium Damaged Kernels (FDK) onto Potato Dextrose Agar (PDA) plates. After 4 to 7 days, pieces of PDA with FHB mycelium are used to inoculate CMC liquid media. The CMC liquid media is aerated for 7 days before a spore count is made. An inoculum of 50,000 spores/ml can be stored at 4° C. for up to 4 weeks.

EXAMPLE II—CROSSES

Sexually crossing two parental genotypes to obtain a segregating, progeny population was done to analyze each offspring plant for the presence of FHB resistance. Specifically, one parent (FHB#37) of Chinese origin demonstrated a high degree of FHB resistance and is the resistant parent. The other parent is an adapted Canadian line (RL4761) expressing desirable agronomic traits but highly susceptible to FHB. It is of note that the susceptible parent may or may not be related to the donor parent.

A population of about 80 doubled haploid (DH) progeny were developed and these offspring represent a random mixing of the two parental genotypes. The production of doubled haploid lines provides the fastest way of obtaining completely homozygous progenies from selected crosses. Also, all the alleles of DH lines are fixed and homozygous and this results in a more reliable assay of quantitative characters than in conventional populations. The advantages of DH lines is discussed in Choo et al.,1985, *Plant Breeding Rev.* 3, 219–252 and Moieni et al., 1997 *Plant Breeding* 116:595–597.

A second segregating population for FHB resistance was developed using the identical procedures as the first population. The resistant parent was the highly resistant Chinese line Sumai3 and the susceptible parent was the high yielding, Canadian adapted line HY368.

As discussed above, hexaploid wheat is comprised of three homoeologous genomes (A, B, and D) each having 7 chromosomes. Procunier et al. 1998 , $9^{th}$ Int. Wheat Gen.Symp., Sask. SK.3:143–147 reported that the D genome ( chromosomes D1 to D7) lacked any significant FHB resistance genes. This placed the resistance genes on the A or B genomes.

Utilizing some of the previously reported literature on the genetic localization of FHB resistance genes, we tested both PCR-based microsatellite and STS markers for linkage to the FHB resistance genes. The molecular markers chosen for testing were on chromosomes:

3BS (Xgwm 389, 264, 285, 533) (Xgwm=wheat microsatellite markers);

3BL (xgwm 340);

1B (STS-1BNOR) (STS=sequence tagged sites; NOR= nucleolus organizer region, rDNA);

1B (1B/1R translocation);

6BS NOR region ( 3 primer sets: FHB For/FHBR2 ; FHB F2/FHB R3; NTS For/18S Rev );

6BL ( Xgwms 626, 219); and

5AL (Xgwm126, 156, 639 and 617)

The FHB#37/RL4761 doubled haploid , segregating population also segregated for the phenotypic marker awnless, and this was also tested for FHB resistance linkage.

EXAMPLE III—GROWTH OF OFFSPRING PLANTS

Offspring plants of the above-described crosses were grown according to methods well-known in the art.

EXAMPLE IV—INOCULATION

Wheat lines are first inoculated at GS 65 (anthesis) and again 4 days later. Approximately 50 ml per line of inoculum is used. The nursery is irrigated for 30 minutes after inoculations are completed.

Wheat heads are inoculated at GS 65 (anthesis) by one of two methods: the spray method or the point method. Using the spray method, the entire head is sprayed with approximately 4 ul of inoculum. Using the point method, 10 ul of inoculum is placed inside one central floret. The plants are placed into a humidity chamber (100% R.H.) for 24 hours. The percentage of infected spikelets is recorded 21 days after inoculation.

There are three types of FHB resistance: Type I—resistance to initial infection; Type II—resistance to hyphal spread within the head; and Type III—lower level of mycotoxin accumulation. Point inoculation measures resistance to spreading (Type II). Spray inoculation measures resistance to initial infection and spreading (Type I and II).

EXAMPLE V—SCORING OF PROGENY

Wheat plots were scored 21 days post-inoculation.

For FHB resistance scoring, two ratings are recorded. Incidence estimates the percentage of heads that have some infection. Severity is the percentage of the infected wheat head that is diseased. The FHB Index is calculated by multiplying the incidence by the severity and dividing by 100.

$$FHB\ index = \frac{Incidence\ (\%) \times Severity\ (\%)}{100}$$

In addition, the morphological phenotype was scored as were the molecular marker phenotypes, as described below.

EXAMPLE VI—LOCALIZATION OF FHB RESISTANCE GENES BY GENETIC MAPPING

The phenotypic scoring for the RL4761 X FHB#37 cross are presented in TABLES 1–2. The results are summarized in FIG. 1 wherein it is shown that there are three FHB resistance genes, Fhb1, located on chromosome 3BS and linked to WMS389 and bcd907a, Fhb2, located on chromosome 6BS and linked to 6B nucleolar organizing region (NOR) and Fhb3, located on chromosome 5AL and linked to the morphological marker awned (B1 locus) and WMS126. The genetic maps of chromosome 3B (FIG. 2), 5A (FIG. 4) and 6B (FIG. 3) show the locations of Fhb1, Fhb3 and Fhb2 respectively in the wheat genome.

EXAMPLE VI—CO-DOMINANT MARKERS FOR FHB RESISTANCE GENES

As discussed above, the most commonly used method for genetic mapping involves the use of RFLP markers. Specifically, this involves isolating DNA from the cell line of interest, digesting the DNA with restriction enzyme(s), running the DNA on an acrylamide or agarose gel, transferring the DNA to a suitable support (Southern blot), hybridizing a labelled probe to the blot, washing the blot and then developing the blot. Despite recent improvements in the individual techniques involved in RFLP mapping, it is still a time-consuming process. Furthermore, for marker assisted selection (MAS) of breeding populations, RFLP markers are not very useful.

An alternative method involves PCR amplification of a DNA target. The specific details of PCR amplification are well known by those knowledgeable in the art and will not be discussed herein. This method has the advantage that the quantity and quality of the DNA is not as important, as the material is amplified during thermal cycling. The material is then run out on an agarose or acrylamide gel, producing a visible DNA band or banding pattern.

Preferably, the DNA band produced is of a given molecular weight for the resistant allele and a different molecular weight for the susceptible allele. These co-dominant markers are the ideal markers since they can distinguish heterozygote plants.

As shown in FIGS. 2–4, the FHB resistance genes have been mapped to their respective chromosomes. Furthermore, Fhb1, Fhb2 and Fhb3 have been localized to genomic regions wherein a number of RFLP and other primers are mapped. These primers were then used in PCR reactions using target DNA from the resistant parent, the susceptible parent and the offspring plants. The primers should be linked to the FHB resistance gene and co-dominant, that is, produce one band from DNA from the susceptible parent and a second band from the resistant parent.

Since it was previously shown that the FHB resistance genes reside on the A and B genomes of wheat, other A and B genomic loci were tested for linkage. However, none of the thirteen A and B loci described in EXAMPLE II showed any association to FHB resistance.

Multiplex PCR is a variant of PCR in which two or more loci are simultaneously amplified in the same reaction. Considerable savings of time and costs can be achieved by this parallel amplification of multiple sequences. In addition, methods must be available for the differentiation of each amplification product within the mixture of all amplification products.

EXAMPLE VII—PCR REACTION PROTOCOL FOR Fhb1 MARKER

The Xgwm389 primers were used as primers in a PCR reaction, described below. In this instance, target DNA was from the resistant parent, FHB#37, the susceptible parent, RL4761 and from the progeny from the cross described above.

Primer amount=100 ng of each primer in a 50 ul PCR reaction.

Fhb1 Forward primer—ATCATGTCGATCTCCTTGACG (SEQ ID No. 1)

Fhb1 Reverse primer—TGCCATGCACATTAGCAGAT (SEQ ID No. 2)

DNA amount=100 ng in a 50 ul PCR reaction.

Thermalcycler Program:

| | Temp: | Time: |
|---|---|---|
| Initial Denaturation | 94° C. | 3:00 |
| 45 cycles of: | | |
| Denaturation | 94° C. | 1:00 |
| Annealing | 64° C. | 1:00 |
| Extension | 72° C. | 2:00 |
| Final Extension | 72° C. | 2:00 |
| Refrigeration | 4° C. | infinite |

Run on 2% Agarose Gel at 80 volts×2.25 hours 175 volt-hours.

Load 20 ul of PCR Product.

The results of the agarose gel electrophoresis are shown on FIGS. 6–7. As can be seen, strains carrying the Fhb1 gene produce a band at a different molecular weight compared to strains not carrying the Fhb1 gene. Specifically: visualization of the agarose gel showed:

~140 bp in FHB resistant parent (93FHB#37).

~120 bp in FHB susceptible parent (RL4761).

As a result, transmission of the Fhb1 gene to progeny can be followed. Furthermore, seed material can be assayed, thereby obviating the need to grow adult plants.

EXAMPLE IX—PCR REACTION PROTOCOL FOR Fhb2 MARKER

The primers used in identifying a marker for Fhb2 are shown in FIG. 5. Specifically, the primer combinations FHB For/FHBR2 and NTS For/18S Rev did not produce a polymorphic signal, whereas the combination of FHBF2/FHBR3 produced a polymorphic signal. Specifically, an additional band at 1.6 kb was visible in the susceptible line that was not present in the resistant donor. A less intense 2.1 kb band was visible in the resistant donor that was not present in the susceptible line on agarose gels as shown in FIGS. 6 and 7. This $Fhb2^R$ allele band was clearly distinguished on a 6% PAGE gel as shown in FIG. 8. The PCR protocol used was similar to that described for the Fhb1 marker discussed above in that:

Primer amount—100 ng of each primer in a 50 ul PCR reaction

Fhb2 Forward primer: TGGTAAAGTCCCTTGMT-GAAA (SEQ ID No 3);

Fhb2 Reverse primer: GCACCGTTTGTTGACCATCAT (SEQ ID No 4)

DNA amount—100 ng in a 50 ul PCR reaction

Annealing temperature—60° C.;

Cycles—32;

Load 20 ul of PCR product;

Run on 1.0% Agarose gel at 80 volts for 4 hours;

Visualizing the agarose gel showed:

2100 bp in FHB resistant parent (93FHB#37);

1600 bp in FHB susceptible parent (RL4761).

This enables transmission of the Fhb2 gene to progeny to be followed.

EXAMPLE X—PCR REACTION PROTOCOL FOR Fhb3 MARKER

The Xgwm126 primers were used as primers in a PCR reaction, as described below. A unique band at about 220 bp was visible in the resistant donor that was not present in the susceptible line, as shown in FIGS. 6 and 7. The susceptible line showed a 200 bp band that was not present in the donor resistant line. These two bands are clearly separated on mini-DNA sequencing gels, as shown in FIG. 9. The PCR protocol used was similar to that described for the Fhb1 and Fhb2 markers discussed above in that:

Primer amount—100 ng of each primer in a 50 ul PCR reaction;

Fhb3 Forward primer: CACACGCTCCACCATGAC (SEQ ID No. 5);

Fhb3 Reverse primer: GTTGAGTTGATGCGGGAGG (SEQ ID No. 6);

DNA amount—100 ng in a 50 ul PCR reaction;

Annealing temperature—61° C.;

Cycles—45;

Load 20 ul of PCR product; and

Run on 2% MetaPhore agarose gel at 120 volts for 4 hours.

Visualization of the agarose gel showed:

220 bp in FHB resistant parent (93FHB#37);

200 bp in FHB susceptible parent (RL4761).

This enables the transmission of the Fhb3 gene to progeny to be followed.

EXAMPLE XI—PCR REACTION PROTOCOL FOR MULTIPLEXING Fhb1, Fhb2 AND Fhb3 MARKERS

The Xgwm389, FHBF2/FHBR3 and Xgwm126 primers were used in a PCR reaction, described below. All six alleles of the three loci can be distinguished on 2% MetaPhore agarose gels as shown in FIG. 7. The three unique susceptible allele bands were present in the susceptible line and absent in the resistant donor line. The resistant donor line showed the three unique resistant allele bands which were absent in the susceptible line. The PCR protocol used was similar to that described for the Fhb1, Fhb2 and Fhb3 markers as discussed above in that:

Primer amount—100 ng of each six primers in a 50 ul PCR reaction;

DNA amount—100 ng in a 50 ul PCR reaction;

Annealing temperature—61° C.;

Cycles—45

Load 20 ul of PCR product

Run on 2% MetaPhore agarose gel at 120 volts for 4 hours.

This enables transmission of the Fhb1, Fhb2 and Fhb3 genes to be tracked simultaneously to progeny.

EXAMPLE XII—DISCUSSION

Three additive FHB resistance genes were identified by PCR-based DNA markers and the precise location of these markers linked to FHB resistance are novel and unreported. The resistance gene Fhb2 is at/near the rDNA locus on chromosome 6BS. The resistance gene Fhb1 is at/near the Xgwm389 locus on chromosome 3BS. The resistance gene Fhb3 is linked to the phenotypic marker awned and at/near the Xgwm126 locus, both located on chromosome 5A.

The Fhb1, Fhb2 and Fhb3 markers could possibly represent portions of the actual Fhb1, Fhb2 and Fhb3 resistance genes. As such, these primers could be used to clone the genes encoding Fhb1 and Fhb2, for example, by screening a cDNA library, reverse transcription of cellular mRNA followed by PCR amplification using the Fhb1 and Fhb2 primers or other methods known in the art. It is of note that the Fhb2 locus (NOR) governs protein synthesis. Microsatellite sequences (Xgwm389, Fhb1; Xgwm126, Fhb3) are located within and immediately adjacent to functional genes.

The markers can be used to test seed material for the presence of FHB resistance genes, thereby obviating the time and expense of growing adult plants for assaying FHB resistance. All six allelic markers can be tested by multiplexing, which is the PCR reaction done in a single tube, described above, and the six allelic products can all be distinguished in a single lane. This saves considerable time and cost. Furthermore, because the test involves PCR amplification followed by gel electrophoresis and visualization of the marker, the test is very user-friendly, easy to do and quick. The markers also allow for gene pyramiding of multiple, independent resistance genes into complex genetic backgrounds.

Furthermore, as the genes for FHB resistance have been localized to specific regions of the wheat genome, it is possible to isolate clones of these genes or subclone these genes into a suitable vector using any of the appropriate techniques known in the art. Specifically, Fhb1, Fhb2 and Fhb3 can be subcloned into a vector or clones containing these genomic regions can be identified for isolating the necessary sequences for expression of the FHB resistance genes under control of the native promoters. As a result of this arrangement, the vector-based Fhb genes would be expressed in wheat cells. The vector may be an integrating plasmid, a replicating plasmid or an artificial chromosome. Furthermore, these vectors would allow for FHB resistance to be transmitted to susceptible plants by transforming the wheat cells with the vector. In addition, given that the FHB resistance genes are additive, it is possible that multiple copies may exert a greater disease resistance.

Alternatively, the Fhb primers described herein may be used in other suitable assays known in the art, for example, RFLP mapping, for following transmission of Fusarium head blight resistance in progeny.

While the preferred embodiments of the invention have been described above, it will be recognized and understood that various modifications may be made therein, and the appended claims are intended to cover all such modifications which may fall within the spirit and scope of the invention.

What is claimed is:

1. A method of detecting Fusarium head blight resistance in a wheat cell, said method comprising:
   providing genomic DNA extracted from the wheat cell;
   providing a primer set selected from the group consisting of:
      primer set A: a forward primer selected from the group consisting of: Forward Fhb1 primer (SEQ ID No. 1), contiguous primers thereof, noncontiguous primers thereof and homologous primers thereof; and a reverse primer selected from the group consisting of: Reverse Fhb1 primer (SEQ ID No. 2), contiguous primers thereof, noncontiguous primers thereof and homologous primers thereof; or
      primer set B: a forward primer selected from the group consisting of: Forward Fhb2 primer (SEQ ID No. 3), contiguous primers thereof, noncontiguous primers thereof and homologous primers thereof; and a reverse primer selected from the group consisting of: Reverse Fhb2 primer (SEQ ID No. 4), contiguous primers thereof, noncontiguous primers thereof and homologous primers thereof; or
      primer set C: a forward primer selected from the group consisting of: Forward Fhb3 primer (SEQ ID No. 5), contiguous primers thereof, noncontiguous primers thereof and homologous primers thereof; and a reverse primer selected from the group consisting of: Reverse Fhb3 primer (SEQ ID No. 6), contiguous primers thereof, noncontiguous primers thereof and homologous primers thereof; or combinations of primer set A, primer set B and primer set C.

combining the genomic DNA and the primer set with reagents suitable for DNA amplification, thereby forming a reaction mixture;

incubating the reaction mixture under conditions wherein the DNA is amplified, thereby producing a DNA fragment of a given molecular weight; and determining the molecular weight of the DNA fragment, wherein use of primer set A results in synthesis of a DNA molecule of a first molecular weight when Fhb1 is present on the genomic DNA or the synthesis of a DNA molecule of a second molecular weight when Fhb1 is absent on the genomic DNA; use of primer set B results in synthesis of a DNA molecule of a third molecular weight when Fhb2 is present on the genomic DNA or the synthesis of a DNA molecule of a fourth molecular weight when Fhb2 is absent on the genomic DNA; and use of primer set C results in synthesis of a DNA molecule of a fifth molecular weight when Fhb3 is present on the genomic DNA or the synthesis of a DNA molecule of a sixth molecular weight when Fhb3 is absent on the genomic DNA.

2. The method according to claim 1 wherein the molecular weights of the DNA fragments are determined by loading the reaction mixture onto a suitable support and electrophoresing the reaction mixture; and visualizing the banding pattern of the DNA fragments, wherein the presence of Fhb1 produces a first banding pattern while the absence of Fhb1 produces a second banding pattern, the presence of Fhb2 produces a third banding pattern while the absence of Fhb2 produces a fourth banding pattern, and the presence of Fhb3 produces a fifth banding pattern while the absence of Fhb3 produces a sixth banding pattern.

3. The method according to claim 1 wherein the wheat cell is a seed.

4. The method according to claim 1 wherein the DNA in the reaction mixture is digested with a restriction enzyme.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Gramineae Triticum

<400> SEQUENCE: 1
atcatgtcga tctccttgac g                                21

<210> SEQ ID NO 2
<211> LENGTH: 20
<212> TYPE: DNA
<213> ORGANISM: Gramineae Triticum

<400> SEQUENCE: 2
tgccatgcac attagcagat                                  20

<210> SEQ ID NO 3
<211> LENGTH: 22
<212> TYPE: DNA
<213> ORGANISM: Gramineae Triticum

<400> SEQUENCE: 3
tggtaaagtc ccttgaatgc aa                               22

<210> SEQ ID NO 4
<211> LENGTH: 21
<212> TYPE: DNA
<213> ORGANISM: Gramineae Triticum

<400> SEQUENCE: 4
gcaccgtttg ttgaccatca t                                21

<210> SEQ ID NO 5
<211> LENGTH: 18
<212> TYPE: DNA
<213> ORGANISM: Gramineae Triticum

<400> SEQUENCE: 5
cacacgctcc accatgac                                    18

<210> SEQ ID NO 6
<211> LENGTH: 19
<212> TYPE: DNA
<213> ORGANISM: Gramineae Triticum

<400> SEQUENCE: 6
gttgagttga tgcgggagg                                   19